US010595822B2

(12) United States Patent
Kajiyama et al.

(10) Patent No.: US 10,595,822 B2
(45) Date of Patent: Mar. 24, 2020

(54) ULTRASONIC-WAVE PROBE, ULTRASONIC-WAVE DIAGNOSIS APPARATUS, AND TEST METHOD OF ULTRASONIC-WAVE PROBE

(71) Applicant: Hitachi, Ltd., Chiyoda-ku, Tokyo (JP)

(72) Inventors: Shinya Kajiyama, Tokyo (JP); Yutaka Igarashi, Tokyo (JP); Yusaku Katsube, Tokyo (JP); Takuma Nishimoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 322 days.

(21) Appl. No.: 15/553,197

(22) PCT Filed: Feb. 25, 2016

(86) PCT No.: PCT/JP2016/055706
§ 371 (c)(1),
(2) Date: Aug. 24, 2017

(87) PCT Pub. No.: WO2016/152375
PCT Pub. Date: Sep. 29, 2016

(65) Prior Publication Data
US 2018/0035974 A1 Feb. 8, 2018

(30) Foreign Application Priority Data
Mar. 25, 2015 (JP) .................. 2015-062295

(51) Int. Cl.
*H04B 17/15* (2015.01)
*H04B 17/29* (2015.01)
*A61B 8/00* (2006.01)

(52) U.S. Cl.
CPC .......... *A61B 8/4444* (2013.01); *A61B 8/4494* (2013.01); *A61B 8/58* (2013.01); *H04B 17/15* (2015.01); *H04B 17/29* (2015.01)

(58) Field of Classification Search
CPC ...... A61B 8/4444; A61B 8/488; A61B 8/4494; A61B 8/58; H04B 17/15; H04B 17/29
See application file for complete search history.

(56) References Cited

U.S. PATENT DOCUMENTS

2012/0092954 A1* 4/2012 Suzuki ............... G01S 7/52017
367/7
2012/0249210 A1 10/2012 Shimizu et al.
(Continued)

FOREIGN PATENT DOCUMENTS

JP 2012-209763 A 10/2012
JP 2013-197929 A 9/2013

OTHER PUBLICATIONS

International Search Report (PCT/ISA/210) issued in PCT Application No. PCT/JP2016/055706 dated Mar. 22, 2016 with English translation (4 pages).
(Continued)

Primary Examiner — Ian J Lobo
(74) Attorney, Agent, or Firm — Crowell & Moring LLP

(57) ABSTRACT

A test for screening defects of a transmission/reception circuit in an IC is enabled at low cost, without withstand voltage violation, and without carrying out electrical contacts with many terminals connected to oscillators. In a transmission/reception separation switch circuit using transistors as switch elements, a potential of a gate is lowered in a test more than the potential in a case of reception to avoid gate-source withstand-voltage violation when a large-amplitude signal is input, and an internal-signal loopback test is carried out without destroying a reception circuit.

15 Claims, 12 Drawing Sheets

(56) References Cited

U.S. PATENT DOCUMENTS

| | | | |
|---|---|---|---|
| 2014/0084997 A1 | 3/2014 | Simmonds | |
| 2015/0374335 A1* | 12/2015 | Brown | A61B 8/4494 |
| | | | 600/447 |
| 2017/0209124 A1* | 7/2017 | Gawazawa | A61B 8/0841 |
| 2017/0326588 A1* | 11/2017 | Broad | A61B 8/4444 |

OTHER PUBLICATIONS

Japanese-language Written Opinion (PCT/ISA/237) issued in PCT Application No. PCT/JP2016/055706 dated Mar. 22, 2016 (3 pages).

* cited by examiner

| Tx/Rx | BYP | VSSHT | Mode |
|---|---|---|---|
| 0 | 0 | 0 | PROHIBITED |
| 0 | 0 | 1 | PROHIBITED |
| 0 | 1 | 0 | PROHIBITED |
| 0 | 1 | 1 | TRANSMISSION |
| 1 | 0 | 0 | PROHIBITED |
| 1 | 0 | 1 | LOOPBACK |
| 1 | 1 | 0 | RECEPTION |
| 1 | 1 | 1 | PROHIBITED |

ULTRASONIC-WAVE PROBE, ULTRASONIC-WAVE DIAGNOSIS APPARATUS, AND TEST METHOD OF ULTRASONIC-WAVE PROBE

TECHNICAL FIELD

The present invention relates to an operation method of a reception/transmission separation switch for separating and protecting a reception circuit, which is formed by a low-voltage device, from a high-voltage signal output from a transmission circuit, which is formed by a high-withstand-voltage device, the switch mounted on an ultrasonic-wave probe, which is a constituent element of an ultrasonic-wave diagnosis apparatus. The present invention particularly relates to the techniques to realize a test method to test the transmission circuit and the reception circuit for each oscillator by using a signal subjected to loopback from the transmission circuit to the reception circuit in the ultrasonic-wave probe.

BACKGROUND ART

An ultrasonic-wave diagnosis apparatus is a non-invasive and highly safe medical diagnostic device for the human body and has a small apparatus scale compared with other medical image diagnosis apparatuses such as an X-ray diagnosis apparatus and a magnetic resonance imaging (MRI) apparatus. In addition, since the apparatus is capable of displaying in real time the state of motion of an examination target such as pulsation of the heart or movement of the fetus by simple operation of simply causing an ultrasonic-wave probe to abut from the body surface, the apparatus plays an important role in the medical care of today.

In the ultrasonic-wave diagnosis apparatus, ultrasonic waves are transmitted into a subject by supplying high-voltage drive signals to each of a plurality of oscillators incorporated in the ultrasonic-wave probe. The reflected waves of ultrasonic waves generated by differences in acoustic impedance of living tissues in the subject are received by each of a plurality of oscillator elements, and images are generated based on the reflected waves received by the ultrasonic-wave probe.

A transmission circuit which supplies high-voltage drive signals to each of the oscillators built in the ultrasonic-wave probe is composed of a high-withstand-voltage device so that high-voltage signals of Vpeak to peak of several tens to a hundred and several tens can be generated. Normally, a device with a structure that relaxes the electric field intensity between a drain and a gate such as laterally diffused MOS (LDMOS) is used for a high-withstand-voltage metal-oxide-semiconductor field effect transistor (MOSFET), and it requires an extremely large area to ensure a drift region between the drain and the gate. Therefore, when the transmission circuit is to be realized as an integrated circuit (IC: Integrated Circuit) on silicon, a large area is required.

On the other hand, since the reflected waves from the living tissues in the subject are affected by attenuation and diffusion in the living body, the amplitude of the reception signal subjected to acoustic-electric conversion by each oscillator is extremely small, and the reception circuit for subjecting this to amplification and signal processing is composed of a low-voltage device for the sake of low noise, low power consumption and small area.

Herein, each of the oscillators in the ultrasonic-wave probe is a transducer in which the same element carries out both of electric-acoustic and acoustic-electric, and both of the transmission circuit for supplying a high voltage to the same element and the reception circuit for receiving minute reception signals are connected. In this case, a switch is normally inserted between the oscillator and the reception circuit so that the reception circuit composed of the low-voltage device is not electrically destroyed when the transmission circuit supplies the high-voltage drive signal to the oscillator. This switch is referred to as a transmission/reception separation switch.

The transmission/reception separation switch becomes a switch-off state in a case of transmission to separate the reception circuit from the high-voltage drive signal generated by the transmission circuit and prevent electrical destruction. It becomes a switch-on state in a case of reception and has a role of causing minute reception signals from the oscillator to pass through with low loss. From the above roles, the transmission/reception separation switch is required to have electrical characteristics that can withstand high-voltage signals, and it is necessary to construct it with a high-withstand-voltage device.

In recent years, an ultrasonic-wave diagnosis apparatus capable of obtaining three-dimensional stereoscopic images has been developed, and examination efficiency can be improved by obtaining a tomographic image by specifying an arbitrary cross section from the three-dimensional stereoscopic image. For three-dimensional image-pickup, the oscillators in the ultrasonic-wave probe have to be changed from a conventional one-dimensional arrangement to a two-dimensional arrangement, and the number of the oscillators is increased to the second power compared with a conventional ultrasonic-wave probe. In this case, since it is practically impossible to increase the number of cables connecting the ultrasonic-wave probe and a main-device body to the second power, reception signals which have undergone reduction by phase-adjustment addition in the ultrasonic-wave probe have to be transferred to the main-body device via the cables. In order to realize the phase-adjustment addition in the ultrasonic-wave probe like this, the functions of transmission/reception and phase-adjustment addition are realized as a beamformer IC, transmission/reception circuits are disposed respectively for the oscillators in the IC to prepare pads electrically connected to the oscillators by one-to-one correspondence, and peripheral pads for transmitting outputs after the phase-adjustment addition to the main-body device are prepared separately from them.

CITATION LIST

Patent Literature

PTL 1: Publication No. US 2014/0084997 A1

SUMMARY OF INVENTION

Technical Problem

FIG. 6 is a perspective view showing an example of a beamformer IC. "100" is a silicon wafer or an IC chip, "200" is an oscillator connecting pad connected to an oscillator (not shown), and "300" is a peripheral pad connected to a main-body-device interface, and the like.

If such an IC is electrically tested in the state of a finished silicon wafer or a chip obtained by dicing a silicon wafer so as to screen a defective chip, probes are required to abut many pads, which are prepared respectively for the oscillators, to connect to a tester. However, as shown in FIG. 6, it is difficult to simultaneously apply a large number of probes to a large number of pads of several thousands or more than ten thousand arranged in two dimensions. Therefore, it is desirable that the test of the transmission/reception circuit for each oscillator is carried out by looping back the signal from the transmission circuit to the reception circuit in the IC. In the case of such an internal-signal loopback test, it suffices to connect to the tester by causing probes to abut about several hundreds of peripheral pads connected to the main-body device, and there is no need to cause the probes to abut several thousands or ten thousands of pads prepared respectively for the oscillators.

From the above, it is a major problem of the ultrasonic-wave probe that the internal-signal loopback test of the transmission/reception circuit disposed for each oscillator is carried out for each channel of the oscillator. When the internal-signal loopback is to be carried out from the transmission circuit to the reception circuit, since the high-voltage signal generated by the transmission signal has a large amplitude, if the signal as it is is caused to pass through the transmission/reception separation switch in the on-state, the part not having a high withstand voltage in the transmission/reception separation switch and the reception circuit composed of a subsequent low-voltage device are electrically destroyed. In order to prevent such destruction, the signal amplitude input to the subsequent reception circuit has to be limited by operating the transmission/reception separation switch in a third state different from a normal transmission state and from a normal reception state, preventing withstand voltage violation in the transmission/reception separation switch, and attenuating the signal looped back therein by the transmission/reception separation switch.

The techniques which enable such an internal-signal loopback test are proposed by PTL 1.

FIG. 14 is FIG. 7 of PTL 1 re-illustrated from the viewpoint of the inventors in order to understand problems of the present invention.

FIG. 14 relates to a transmission/reception separation switch using a MOS on a triple well. "1401" is a processor for transmitting/receiving signals, "1402" is a transmission circuit, and "1403" is a power amplifier for transmission. RFIO is a terminal for transmission and reception. In the reception side, "1404" and "1405" are transmission/reception separation switches, "1406" is an attenuator, "1407" and "1408" are amplifiers, and "1409" is a reception circuit.

In the example shown in FIG. 14, normal reception is an operation of amplifying the output of the transmission/reception separation switch 1404 having a small loss by a low noise amplifier (LNA: Low Noise Amplifier) 0 (1407); and, in internal-signal loopback calibration, reception is carried out by the signal path of LNA1 (1408) passed through the attenuator 1406 subsequent to the transmission/reception separation switch 1405, thereby avoiding destruction of the reception circuit 1409.

By virtue of this configuration, a low noise receiver can be formed by using a low-loss switch in the case of reception; and, in the case of internal-signal loopback calibration, the signal amplitude can be limited by the attenuator to prevent destruction of the reception circuit.

However, for the purpose of screening defects by the test of LNA0 used in the actual reception operation, the signal path which is amplified by LNA0 also in the case of internal-signal loopback has to be selected. Even if the operation of LNA1 is tested by the signal path amplified by LNA1, it does not mean that LNA0 has been tested. Moreover, if an attenuator is disposed in front of LNA0 so that LNA0 is not destroyed and an internal-signal loopback test is to be carried out, the attenuator is inserted in series in the signal path. Therefore, increase in the loss and the noise index in a normal receiving operation are inevitable. Furthermore, in the configuration of FIG. 14, it is necessary to prepare circuits for two paths for normal reception and for internal-signal loopback, and there is also a problem that the circuit area is increased.

From this point, for the purpose of testing for screening a defective chip, it is necessary to operate the circuit itself responsible for actual transmission/reception operations and to carry out an internal-signal loopback test which does not destroy the device.

The above and other objects and novel characteristics of the present invention will become apparent from the description of this description and accompanying drawings.

Solution to Problem

A summary of representative ones of the invention disclosed in the present application will be briefly described as follows. A switch-off state is obtained in a case of transmission, wherein a reception circuit is separated from a high-voltage drive signal generated by a transmission circuit to prevent electric breakdown; and a switch-on state is obtained in a case of reception, wherein a minute reception signal from an oscillator is caused to pass through with low loss in a transmission/reception separation switch circuit; wherein, in an internal-signal loopback test from the transmission circuit to the reception circuit, a gate-source voltage Vgs of high-withstand-voltage MOS constituting a switch is lowered than that in a case of normal reception. More preferably, a low-voltage MOS is connected between a switch output and 0-V GND or a predetermined power source and is turned on in the internal-signal loopback test.

As described above, by using a basic switch circuit mutually connecting gates and sources of two widely-known high-withstand-voltage MOSs, circuit operations in which gate-source withstand voltage violation does not occur even when a loopback signal having a large signal amplitude is received from the transmission circuit can be realized, and, furthermore, the signal can be attenuated by voltage dividing by an on-resistance of the transmission/reception separation switch and a low-voltaqe MOS on-resistance between the switch output and GND. Therefore, the internal-signal loopback test of the transmission/reception circuit can be carried out without destroying the reception circuit formed by a subsequent low-voltage device.

The transmission/reception separation switch is provided with a function of signal attenuation without providing an attenuator on a reception signal path. As a result, there is no need to separate a signal path of normal reception and a signal path in a case of internal-signal loopback like PTL 1, and the operations of the transmission/reception circuit per se, which carries out actual transmission/reception operations, can be tested by internal-signal loopback. Also, the gate-source voltage Vgs of the MOS constituting the transmission/reception separation switch is changed in the case of reception and in the case of internal-signal loopback test. As a result, in the case of reception, Vgs is biased to a vicinity of a maximum withstand voltage to realize the reception circuit with a low on-resistance, in other words, low loss and low noise, and, on the other hand, the withstand voltage is ensured so as not to destroy the device in the internal-signal loopback test, wherein high reception performance and high testability are both enabled.

Another aspect of the present invention is an ultrasonic-wave probe having an oscillator, a transmission circuit connected to the oscillator, a reception circuit connected to the oscillator, and a transmission/reception separation switch disposed between the oscillator and the reception circuit. The transmission/reception separation switch has two transistor elements, and gates and sources of the two transistor elements are mutually connected. A gate-potential step-down circuit for lowering the voltage Vgs between the common gate and the common source of the two transistors is provided. When a test signal is input to the transmission circuit and the test signal is to loopback from the transmission circuit to the reception circuit, a gate potential of the transistor is stepped down to cause the test signal to pass through while ensuring the voltage Vgs between the common gate and the common source, the voltage which does not violate a gate-source withstand voltage of the transistor.

In order to control the gate potential of the transistor, for example, it is conceivable to subject a power-supply voltage (or a voltage of an input signal of the switch) to voltage dividing by a resistance. Alternatively, a method of voltage step-down utilizing, for example, a diode or a diode-connected transistor can be employed. By carrying out the control thereof in association with loopback of the test signal, a test mode can be realized in addition to a transmission/reception mode.

As a further preferred specific example, an output-side transistor is connected to a switch output of the transmission/reception separation switch, and a connection destination of the output-side transistor is GND of 0 V or a power source corresponding to a center voltage of a signal applied to an input in a switch-on state. Then, by short-circuiting the switch output to GND or to the power source corresponding to the center voltage via the output-side transistor, the input signal voltage of the transmission/reception separation switch is divided by the on-resistance of the transmission-reception separation switch and the on-resistance of the output-side transistor, and the signal amplitude thereof is attenuated.

Another aspect of the present invention is an ultrasonic-wave diagnosis apparatus having a sub array, an adder circuit configured to add an output from the sub array, and a main-body device configured to process an output from the adder circuit. The sub array includes a plurality of oscillator channels; and each of the oscillator channels has an oscillator, a transmission circuit connected to the oscillator, a reception circuit connected to the oscillator, and a transmission/reception separation switch. The transmission/reception separation switch has a transistor as a switching element and has a potential control circuit for controlling a gate-source voltage Vgs of the transistor. The switch has: a transmission mode to cause the transmission/reception separation switch to be in an off-state in a case of transmission in which a signal from the transmission circuit is input to the oscillator; a reception mode to cause the transmission/reception separation switch to be in an on-state in a case of reception in which a signal is input from the oscillator to the reception circuit; and a test mode to set the gate-source voltage Vgs of the transistor to a potential different from the potential in the transmission mode and the potential in the reception mode by the potential control circuit.

Another aspect of the present invention is a test method of an ultrasonic-wave probe having an oscillator, a transmission circuit connected to the oscillator, a reception circuit connected to the oscillator, and a transmission/reception separation switch disposed between the oscillator and the reception circuit. The transmission/reception separation switch has two transistor elements and is configured to mutually connect a gate and a source of the two transistor elements; and the switch has: a transmission mode to cause the transmission/reception separation switch to be in an off-state in a case of transmission in which the oscillator is driven by the transmission circuit; a reception mode to cause the transmission/reception separation switch to be in an on-state in a case of reception in which a signal from the oscillator is input to the reception circuit; and a test mode to set the voltage Vgs between the common gate and the common source of the two transistors at the middle between the voltage in the transmission mode and the voltage in the reception mode.

Advantageous Effects of Invention

The internal-signal loopback test method in which the signal is attenuated and output while ensuring the withstand voltage in the transmission/reception separation switch so that the subsequent low-voltage reception circuit is not destroyed can be realized.

The problems, configurations, and effects other than those described above will be clarified from the description of the embodiments below.

DESCRIPTION OF EMBODIMENTS

Figure 1:
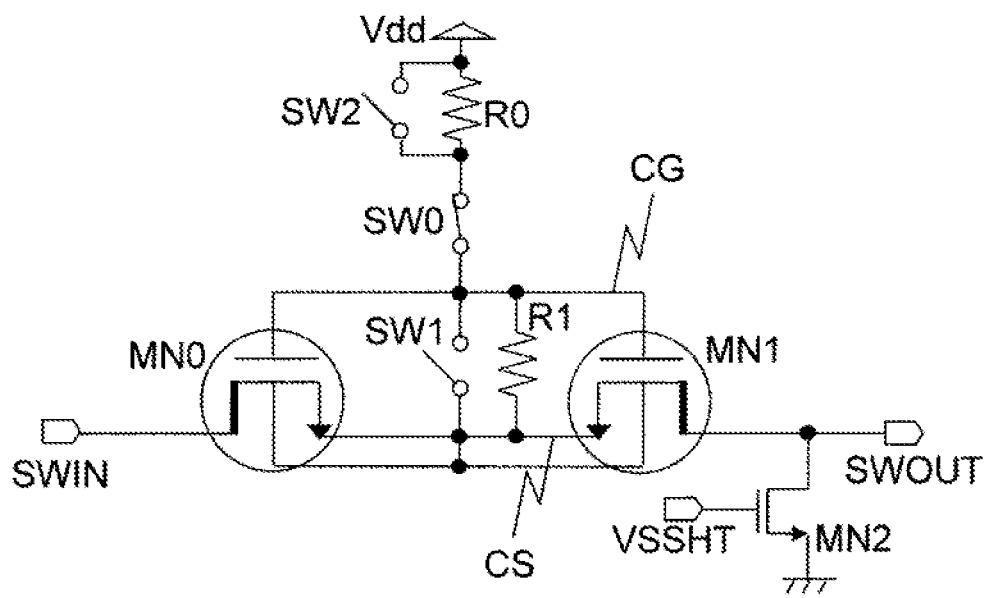
FIG. 1 is a circuit diagram showing a circuit configuration for generating Vgs of a high-withstand-voltage NMOS by resistance voltage dividing as an example of an embodiment of the present invention.

Hereinafter, embodiments will be described in detail with reference to the drawings. However, the present invention is not construed as being limited to the description of the embodiments described below. Those skilled in the art can easily understand that specific configurations can be changed without departing from the spirit or gist of the present invention.

In the configuration of the invention described below, the same reference signs are used for the same parts or parts having similar functions in different drawings, and redundant-explanation may be omitted.

The notations such as "first", "second", "third", and the like in the present description, and the like are attached to identify constituent elements, and do not necessarily limit the number or order. In addition, the numbers for identifying the constituent elements are used for each context, and the number used in one context, does not necessarily indicate the same constitution in other contexts. Also, it does not preclude that a constituent element identified by a certain number also serves as the function of a constituent element identified by another number.

The positions, sizes, shapes, ranges, and the like of the respective components shown in drawings, and the like may not show actual positions, sizes, shapes, ranges, and the like in order to facilitate understanding of the invention. Therefore, the present invention is not necessarily limited to the positions, sizes, shapes, ranges, and the like disclosed in the drawings, and the like.

FIG. 1 shows a configuration of an embodiment of the present invention. A basic switching circuit with two high-withstand-voltage NMOSs (N-channel enhancement type metal-oxide-semiconductor field-effect transistors (MOSFETs)) in which a gate and a source of MN0 and MN1 in FIG. 1 are connected to each other in series is widely known as a publicly known circuit. Although not particularly limited, it is assumed that a potential is determined outside the configuration of FIG. 1, for example, by connecting a switch input SWIN and a switch output SWOUT of FIG. 1 to GND of 0 V via a resistance.

Herein, circled MN0 and MN1 in FIG. 1 are high-withstand-voltage MOSs. In general, a device with a structure that relaxes the electric field intensity between a drain and a gate, such as LDMOS, is used for the high-withstand-voltage MOS, and an extremely large area is required to ensure a drift region between the drain and the gate. The LDMOS has a structure in which the source and the drain are asymmetric, and the source and the bulk are connected. The structure between the drain and the gate and between the drain and the source can withstand a high voltage such as several tens V or 100 V or more, but only a low voltage such as 5 V can be applied between the gate and the source. In FIG. 1, for example, the line on the left side of the symbol of MN0 is thickened, which means that the left side is the drain in terms of structure and there is a drift region for relaxing electric fields.

If the potentials of SWIN and SWOUT are determined to be 0 V from the outside when a switch SW0 in FIG. 1 is on, SW1 is off, and SW2 is on, a potential VCG of a common gate CG becomes equal to Vdd, and the voltage between the gate and the source of MN0 and MN1 is Vdd. MN2 is a transistor connected to a switch output of a transmission/reception separation switch. This transistor may be a low-voltage transistor. A connection destination of the transistor MN2 is GND of 0 V or a power source corresponding to a center voltage of a signal applied to the input in a switch-on state. In this manner, by short-circuiting the switch output to GND or to the power source corresponding to the center voltage via the transistor MN2, the input, signal voltage of the transmission/reception separation switch is divided by the on-resistance of the switch and the on resistance of the transistor MN2, and the signal amplitude thereof is attenuated. More specifically, VSSHT is lowered to a low level to turn off MN2, and a state of "Vgs of MN0, MN1"=VCG=Vdd is assigned to a receiving operation, and a high gate-source voltage Vgs of MN0 and MN1 near a withstand voltage is applied; as a result, a low on-resistance can be realized as the transmission/reception separation switch, and reception performance with low loss and low noise can be obtained.

On the other hand, when the switch SW0 is on, SW1 is off, and SW2 is off, the potential VCG of the common gate CG becomes the potential obtained by dividing Vdd by R0 and R1 (Mathematical Expression 1).

$$VCG = Vdd \cdot \frac{R1}{R0 + R1} \qquad \text{[Mathematical Expression 1]}$$

This VCG is applied as Vgs of MN0 and MN1, and MN0 and MN1 are turned on with a lower voltage than that of reception and with a high resistance. This state is assigned to an internal-signal loopback test mode.

When a pulse signal having a large amplitude is input to the transmission/reception separation switch from a transmission circuit in a reception state, for example, if the gate-source withstand voltage of MN0 and MN1 is 6 V and Vdd is 5 V, −2 V is input as a low level of the pulse signal. As a result, a potential VCS of a common source CS becomes −2 V, 7 V which is higher than the withstand voltage is applied as Vgs between the gate and source of MN0 and MN1, and MN0 and MN1 are destroyed. However, in the state in which SW2 is turned off, Vgs becomes low since it is determined by the voltage division ratio according to R0 and R1 of Vdd, wherein −2 V from the transmission circuit can be received by appropriately taking the ratio of R0 and R1. For example, if R0=R1, even if −2 V is input from the transmission circuit, only 3.5 V, which is half of 7 V, is applied to Vgs, and operation can be carried out within the withstand voltage.

Furthermore, if VSSHT is caused to be a high level in the internal-signal loopback test to turn on MN2, the signals can be subjected to voltage division and attenuated by MN0, MN1, and MN2. On the assumption that an cm-resistance of MN* is RMN*, an input signal voltage is VIN, and an output signal voltage is VOUT, (Mathematical Expression 2) is obtained.

$$VOUT = VIN \cdot \frac{RMN2}{RMN0 + RMN1 + RMN2} \qquad \text{[Mathematical Expression 2]}$$

Herein, in the state of the internal-signal loopback test mode in which SW2 is turned off as shown in FIG. 1, Vgs of MN0 and MN1 is lower than that in the case of reception, and, since on-resistances RMN0 and RMN1 are higher, the output amplitude thereof can be further reduced by increasing the denominator of the above described expression.

From the above, by preparing the internal-signal loopback test mode in FIG. 1 in which SW0 is turned on, SW1 is turned off, and SW2 is turned off and causing Vgs of MN0 and MN1 to be lower than that in the case of reception by resistance voltage division, the on-resistances of MN0 and MN1 are increased to be higher than those in the case of reception, and MN2 is turned on. As a result, it is possible to receive a large-amplitude internal loopback signal without causing a withstand voltage violation, to attenuate the signal to a signal amplitude that does not destroy a subsequent low-voltage reception circuit by voltage division, and to output the signal. In addition, since the transmission/reception separation switch per se is used as an attenuator, there is no need to prepare an attenuator separately from the transmission/reception separation switch like PTL 1. Furthermore, since the same signal path is used in the case of reception and in the case of internal-signal loopback test, a test can be carried out for the reception circuit per se used for the actual receiving operation. In the case of transmission, SW0 is turned off, SW1 is turned on, and MN0 and MN1 are turned off, thereby turning off the transmission/reception separation switch.

First Embodiment

Figure 2:
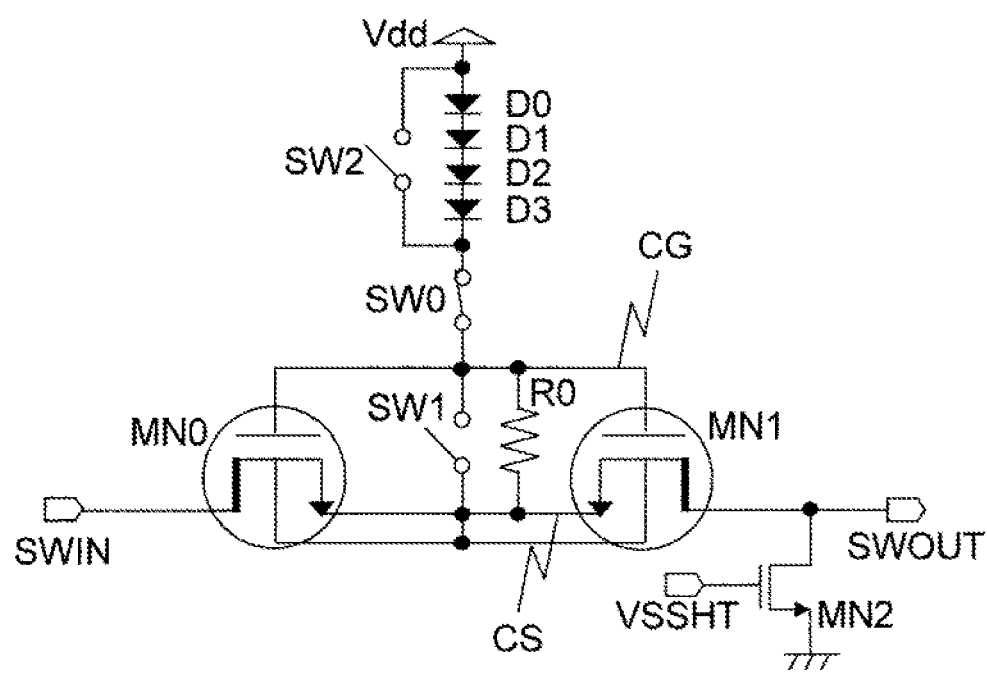
FIG. 2 is a circuit diagram showing a circuit configuration for generating Vgs of the high-withstand-voltage NMOS with serially-connected forward diodes as a first embodiment instead of the resistance voltage dividing of FIG. 1.

FIG. 2 shows an embodiment of the transmission/reception separation switch according to the present invention. In the configuration of FIG. 1, Vgs of MN0 and MN1 is generated by resistance voltage division by the resistance voltage division of R0 and R1. Since current flows from Vdd to R0 and R1 at this time, for example, in order to suppress the power consumption to the order of µW, it is necessary to set R0 and R1 to high resistances of the order of MΩ; and, although it depends on the sheet resistance of the resistance type prepared in a semiconductor process used, there is a concern that the area of the resistance increases.

Therefore, in the first, embodiment shown in FIG. 2, forward diodes D0, D1, D2, and D3 are used instead of R0 in FIG. 1. The internal-signal loopback test mode is obtained by turning SW0 on, SW1 off, and SW2 off, the forward voltage of the diodes at this point is Vf, and the potential of the common gate CG becomes (Mathematical Expression 3).

$$VCG = Vdd - 4 \cdot Vf \qquad \text{[Mathematical Expression 3]}$$

VCG falls from Vdd by Vf of the diodes in four stages. The number of serial stages of the forward diodes may be adjusted according to the required VCG. Since a current is passed through the diodes to generate Vf, a resistance R0 or a current source is required between CG and CS. In the semiconductor process used, if diodes with small areas that can be used in the forward direction are prepared, there is a higher possibility in the present embodiment that a circuit area can be reduced than in the configuration of FIG. 1.

Second Embodiment

Figure 3:
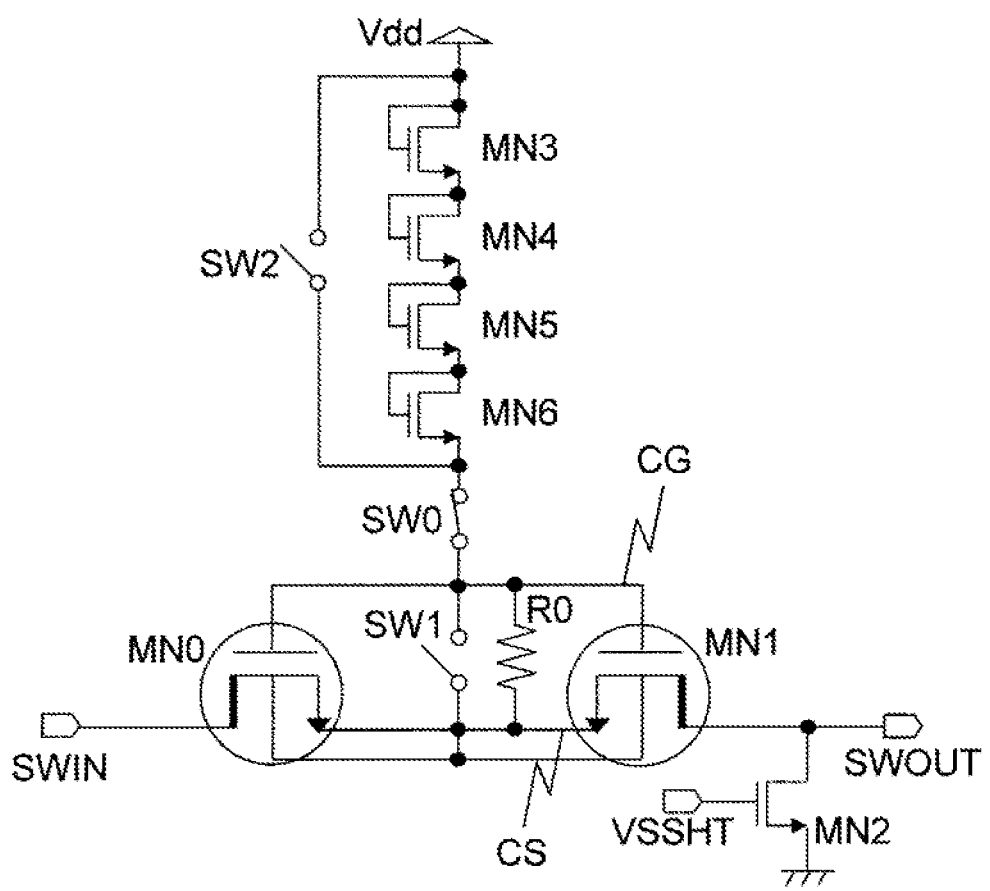
FIG. 3 is a circuit diagram showing a circuit configuration for generating Vgs of a high-withstand-voltage NMOS by series connection of diode-connected NMOSs connecting drains and gates to each other as a second embodiment, in place of the resistance voltage dividing of FIG. 1.

FIG. 3 shows an embodiment of the transmission/reception separation switch according to the present invention. In the first embodiment of FIG. 2, the forward diodes are used to lower the potential VCG of the common gate CG from Vdd. However, depending on the semiconductor process, diodes usable in the forward direction are designed on the assumption that a large current for rectification is to flow therethrough, and the area thereof may be large.

Therefore, in the second embodiment shown in FIG. 3, diode-connected MGSs in each of which a drain and a gate are connected to each other are used instead of the diodes of the first embodiment. The internal-signal loopback test mode is obtained by turning SW0 on, SW1 off, and SW2 off, gate-source voltages of MN3, MN4, MR5, and MN6 at this point are Vgsd, and the potential of the common gate CG becomes (Mathematical Expression 4).

$$VCG = Vdd - 4 \cdot Vgsd \qquad \text{[Mathematical Expression 4]}$$

VCG falls from Vdd by Vgsd of the diode-connected MOSs in four stages. The number of serial stages of the diode-connected MOSs may be adjusted according to the required VCG. Since a current is passed through the diode-connected MOSs to generate Vgsd, a resistance R0 or a current source is required between CG and CS. In the semiconductor process used, if resistive elements with high sheet resistances or diodes with small areas that can be used in the forward direction are not prepared, there is a higher possibility in the present embodiment that the circuit area can be reduced than in the configuration of FIG. 1 or the first embodiment of FIG. 2.

Third Embodiment

Figure 4:
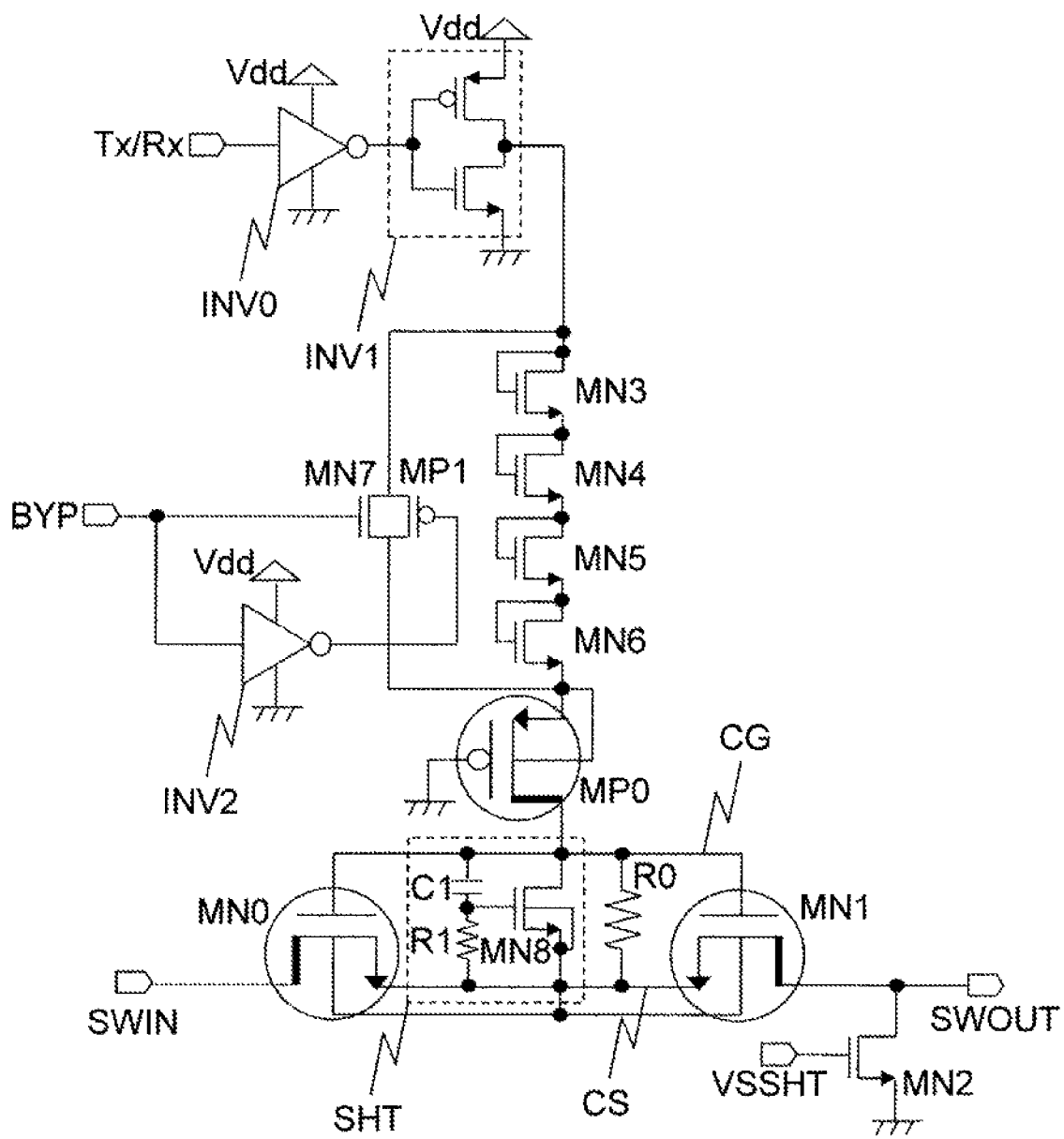
FIG. 4 is a circuit diagram showing a circuit configuration in which an ideal switch in the embodiment of FIG. 3 is expressed by actual elements.

FIG. 4 shows a different embodiment of the transmission/reception separation switch according to the present invention. In this embodiment, the elements expressed as ideal switches in FIGS. 1, 2, and 3 are realized by actual MOSs. SW0 in FIG. 3 is replaced by MP0 in FIG. 4, SW1 in FIG. 3 is replaced by SHT in FIG. 4, and SW2 in FIG. 3 is replaced by MN7 and MP1 in FIG. 4.

In a case of transmission, the transmission circuit outputs high-voltage pulses of positive voltages or negative voltages; wherein, in a case in which a negative voltage is output, SWIN becomes a negative voltage, the drain in the structure of MN0 electrically serves as a source, and MN0 is turned on to be low to lower CS to a negative voltage. Therefore, CS and CG swing between the negative voltage and 0 V in the case of transmission. Therefore, a PMOS with a high withstand voltage has to be used as MP0 for switching the operations of transmission and reception. Also, the circuit connected to the source side of MP0 can be formed by using a low-voltage MOS since it is protected by MP0.

SHT in FIG. 4 is a shunt circuit and operates as a switch for turning off MN0 and MN1 in the case of transmission. MN8 is normally off since a gate and a source thereof are connected to each other via R1. When the transmission circuit transmits a negative voltage, SWIN and CS are driven to negative voltages, the voltage between CG and CS increases at a certain slew rate or higher, C1 follows this to turn on MN8 and short-circuit CG and CS. As described above, when Vgs of MN0 and MN1 is increased at the certain slew rate or higher, the gates and the sources thereof are short-circuited to obtain Vgs=0 V, that, is, the off-state as the transmission/reception separation switch can be ensured.

Figures 5, 6:
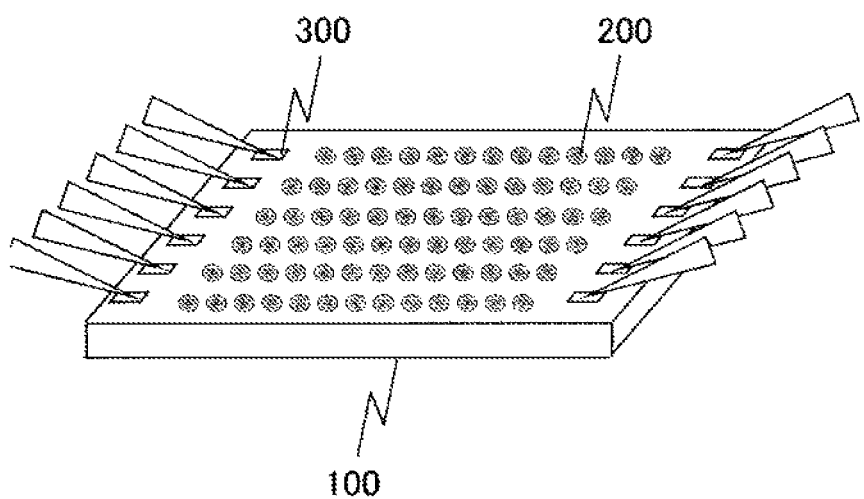
FIG. 5 is a table diagram of a truth-value table expressing relations between operation modes and control signals of the circuit configuration by the actual elements of FIG. 4.
FIG. 6 is a perspective view showing a test configuration of an IC in a state of a silicon wafer or a chip after dicing.

FIG. 5 is a truth-value table related to each mode state of the second embodiment of FIG. 4. In FIG. 4, Tx/Rx is a transmission/reception switching signal, BYP is a bypass signal of a gate step-down circuit, and VSSHT is a gate control signal of a low-voltage NMOS gate control signal which short-circuits the output to GND. In the case of transmission, in other words, when Tx/Rx is at a low level and BYP and VSSHT are at a high level, an inverter INV1 outputs a low level, this passes through a bypass switch of MN7 and MP1 and gives 0 V to the source of MP 0, and MP0 is turned off. MN0 and MN1 constituting the switch are subjected to gate-source short-circuiting constantly by R0 and transiently by SHT and become an off-state. MN2 is turned on to suppress AC signal leakage to the output due to parasitic capacity coupling in the case of transmission and improve isolation performance.

In the case of reception, in other words, when Tx/Rx and BYP are at a high level and VSSHT is at a low level, the inverter INV1 outputs a high level, this passes through the bypass switch of MN7 and MP1 and gives Vdd to the source of MP0, and MP0 is turned on, Vdd is applied as the gate-source voltage Vgs of MN0 and MN1 constituting the switch, high Vgs is applied thereto, and it is turned on as the transmission/reception separation switch with a low on-resistance. MN2 is turned off so that there is no loss of the received signal.

In the internal-signal loopback test, in other words, when Tx/Rx is at a high level, BYP is at a low level, and VSSHT is at a high level, the inverter INV1 outputs the high level Vdd, and, since MN7 and MP1 are off, the potential stepped-down from Vdd by diode-connected low-voltage NMGSs of MN3, MN4, MN5, and MN6 is applied to the source of MP0. This is transferred by MP0, and the same potential stepped down from Vdd is also applied to a node of CG. More specifically, the gate-source voltage Vgs of MN0 and MN1 constituting the switch is lower than that in the case of reception, and MN0 and MN1 are turned on with high resistances. Since MN2 is on, the internal loopback signal input from SWIN can be subjected to voltage-division and attenuated by MN0, MN1, and MN2 and be output to the subsequent low-voltage reception circuit with a small amplitude.

FIG. 6 shows a test configuration of a beamformer IC in an ultrasonic-wave probe having 2-dimensional array oscillators applied to the present invention in a state of a silicon wafer or in a state of an IC chip after dicing. The number of pads 200 connected to the oscillators (not shown) varies from several thousands to over ten thousand or more in a chip 100, and the number of the pads is too large. Therefore, it is difficult to cause probes to contact all of them to test transmission/reception circuits in the IC one channel at a time by a tester. Therefore, by looping back signals from the transmission circuit to the reception circuit in the IC to carry out tests and taking out addition outputs from peripheral pads of a main-body device interface, test results can be monitored by the tester or the main-body device, and defective products of the IC can be subjected to screening.

Figure 7:
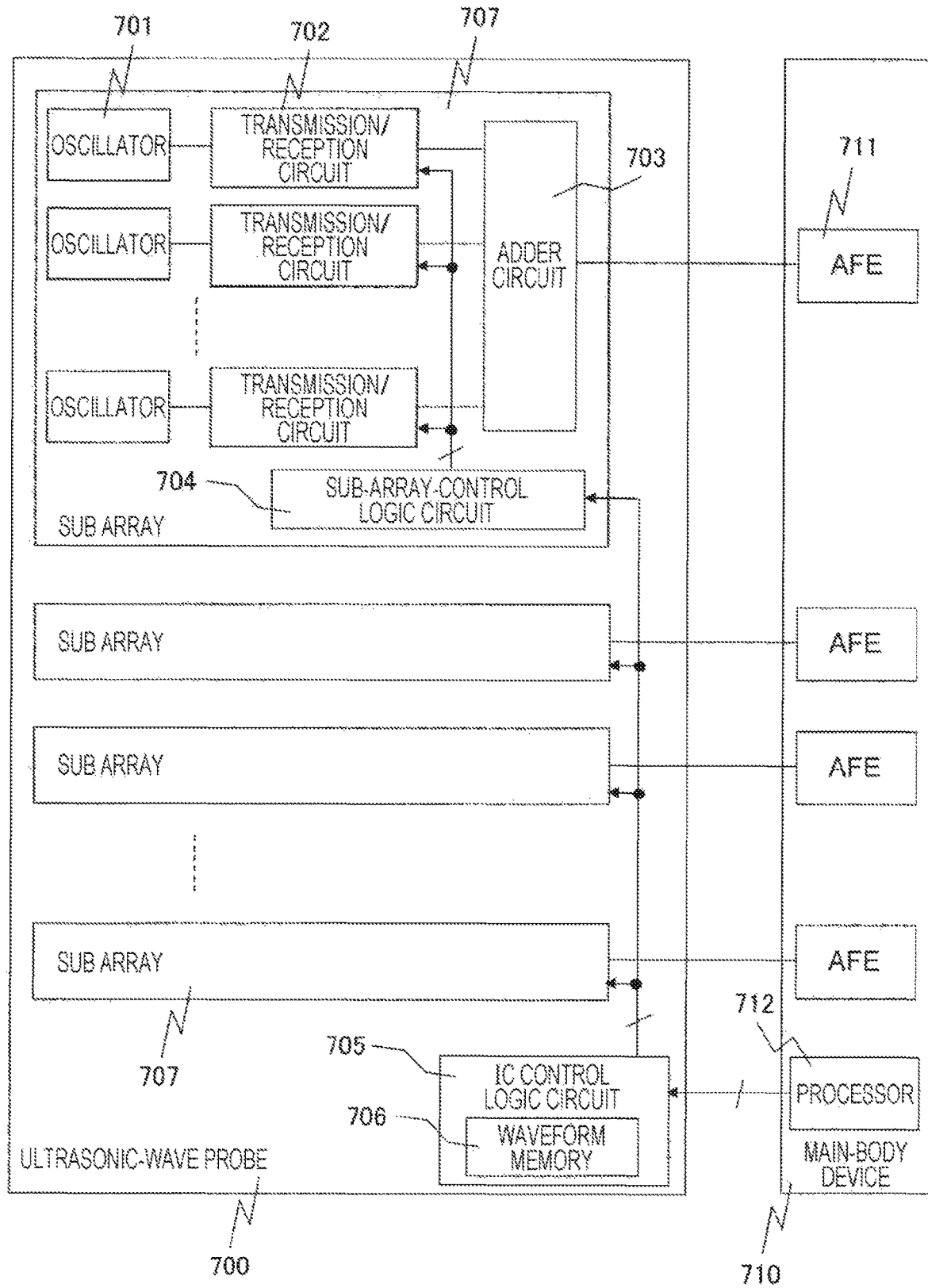
FIG. 7 is a block diagram showing a system configuration example of an ultrasonic-wave diagnosis apparatus to which the present invention is applied.

FIG. 7 shows the ultrasonic-wave probe having the 2-dimensional array oscillators for 3-dimensional image pickup and a system configuration to which the present invention is applied. In the ultrasonic-wave probe 700, transmission/reception circuits 702 are disposed respectively for the oscillators 701, and reception outputs are added by an adder circuit 703 and transmitted to an analog front end (AFE) 711 of the main-body device 710. A grouping unit of oscillator channels to be subjected to addition is referred to as a sub array 707. For example, in each of the sub arrays 707, the transmission/reception circuits 702, the adder circuit 703, a sub-array-control logic circuit 704, and the like are formed by a single chip as shown in FIG. 6. The oscillator connecting pad 200 shown in FIG. 6 is connected to the oscillators 701.

A processor 712 in the main-body device 710 transmits control signals to a control logic circuit 705 of the IC in the ultrasonic-wave probe, and the IC control logic circuit 705 carries out control such as switching of transmission/reception in response thereto. For example, the scale of the IC control logic circuit and the number of control signals in the IC can be reduced by controlling transmission/reception switching related to the control of the transmission/reception separation switch collectively by each sub array. Alternatively, as shown in FIG. 7, it is possible to dispose sub-array-control logic circuits respectively for the sub arrays, hierarchize control, and independently control each of the transmission/reception circuits from the sub-array-control logic circuit by granularity. Although not particularly limited, if the transmission circuit is not a linear amplifier method but a pulsar method, waveforms are transmitted to a pulsar as digital values; therefore, the IC control logic circuit 705 includes a waveform memory 706 which stores the waveform data transmitted by the pulsar.

Figure 8:
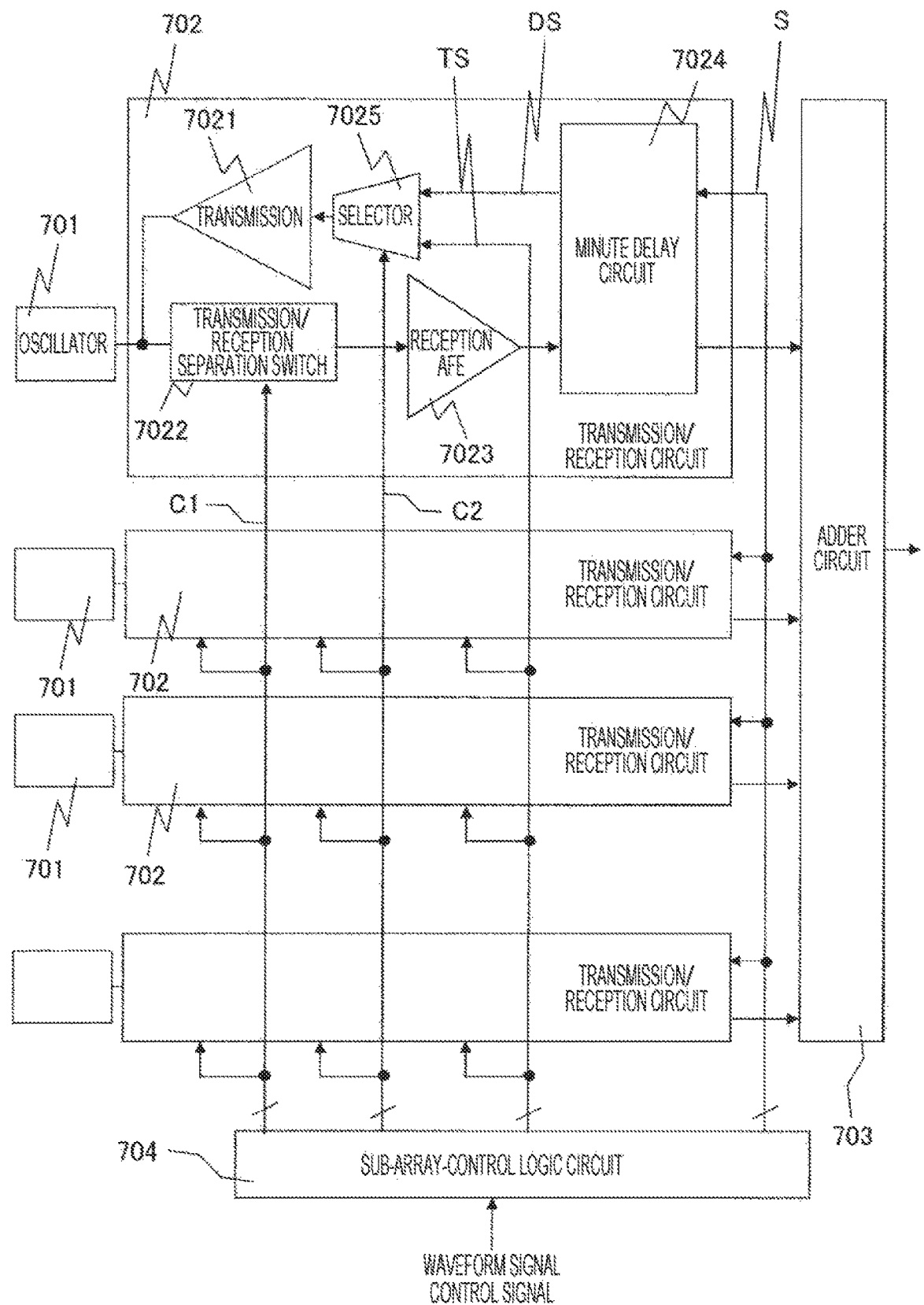
FIG. 8 is a block diagram showing a sub array configuration example of an IC in the ultrasonic-wave probe to which the present invention is applied.

FIG. 8 shows details of the configuration in the sub array 707. The transmission/reception circuit 702 for each oscillator includes a transmission circuit 7021 which is formed of a high-withstand-voltage MOS and generates a high-voltage signal to drive the oscillator 701, a transmission/reception separation switch 7022 according to the present invention, a reception analog front end 7023 of a low voltage system, and a minute delay circuit 7024 which delays transmission signals to carry out beam forming and delays reception signals to carry out phase adjustment. The reception signals, which have undergone phase adjustment by the minute delay circuit 7024, are subjected to addition by the adder circuit 703 and transmitted to the main-body device 710. In the sub array, a plurality of sets of the oscillators 701 and transmission/reception circuits 702 are present. One oscillator and a transmission/reception circuit connected thereto constitute one oscillator channel.

In the configuration of FIG. 8, the minute delay circuit 7024 is used for ultrasonic-wave beam forming by focusing in the case of transmission and is used for phase-adjustment addition in the case of reception. Although the same circuit is used for both transmission and reception, since the transmission circuit and the reception circuit are required to operate at the same time in the internal-signal loopback test, the operation in the internal-signal loopback test of the minute delay circuit has to be assigned to either operation or reception. In FIG. 8, the minute delay circuit 7024 is carrying out a reception operation in the internal-signal loopback test. In the case of normal transmission, a waveform signal S is input to the minute delay circuit, is delayed by the minute delay circuit, and is transmitted by the transmission circuit 7021 as a delayed waveform signal DS. However, in the internal-signal loopback test, a loopback-test waveform signal TS from the sub-array-control logic circuit 704 is selected by a selector 7025 provided before the transmission circuit and is input to the transmission circuit 7021. The transmitted signal is input to the transmission/reception separation switch 7022 in the internal-signal loopback test mode, is attenuated to have a small amplitude, and is input to the reception AFE 7023. Furthermore, the signal is delayed by the minute delay circuit 7024, is added to the signals of the other oscillator channels, and is output from the sub array 707. No signal is input to the oscillator channels which are not test targets of the sub array so that they output no signals. As a result, the output from the transmission/reception circuit of the oscillator channel serving as a test target can be obtained as an output of the adder circuit. Therefore, the single channel of the oscillator can be tested. More specifically, the transmission circuit 7021, the reception circuit 7023, and the minute delay circuit 7024 can be tested. Note that C1 is a control signal of the transmission/reception separation switch 7022, and C2 is a control signal of the selector 7025.

In the ultrasonic-wave diagnostic apparatus, a B-mode in which the intensity of reflected signals is converted into luminance to form images and a mode in which Doppler signals are expressed by colors are prepared; wherein, the transmission amplitude in a continuous-wave (CW: Continuous Wave) Doppler mode for measuring high-speed blood flows is normally the smallest. Therefore, although not particularly limited by this, in internal-signal loopback test, carrying out transmission by the transmission circuit in the CW mode is advantageous in terms of gate-source withstand-voltage ensuring of the transmission/reception separation switch and protection of the subsequent low-voltage reception AFE.

Figure 9:
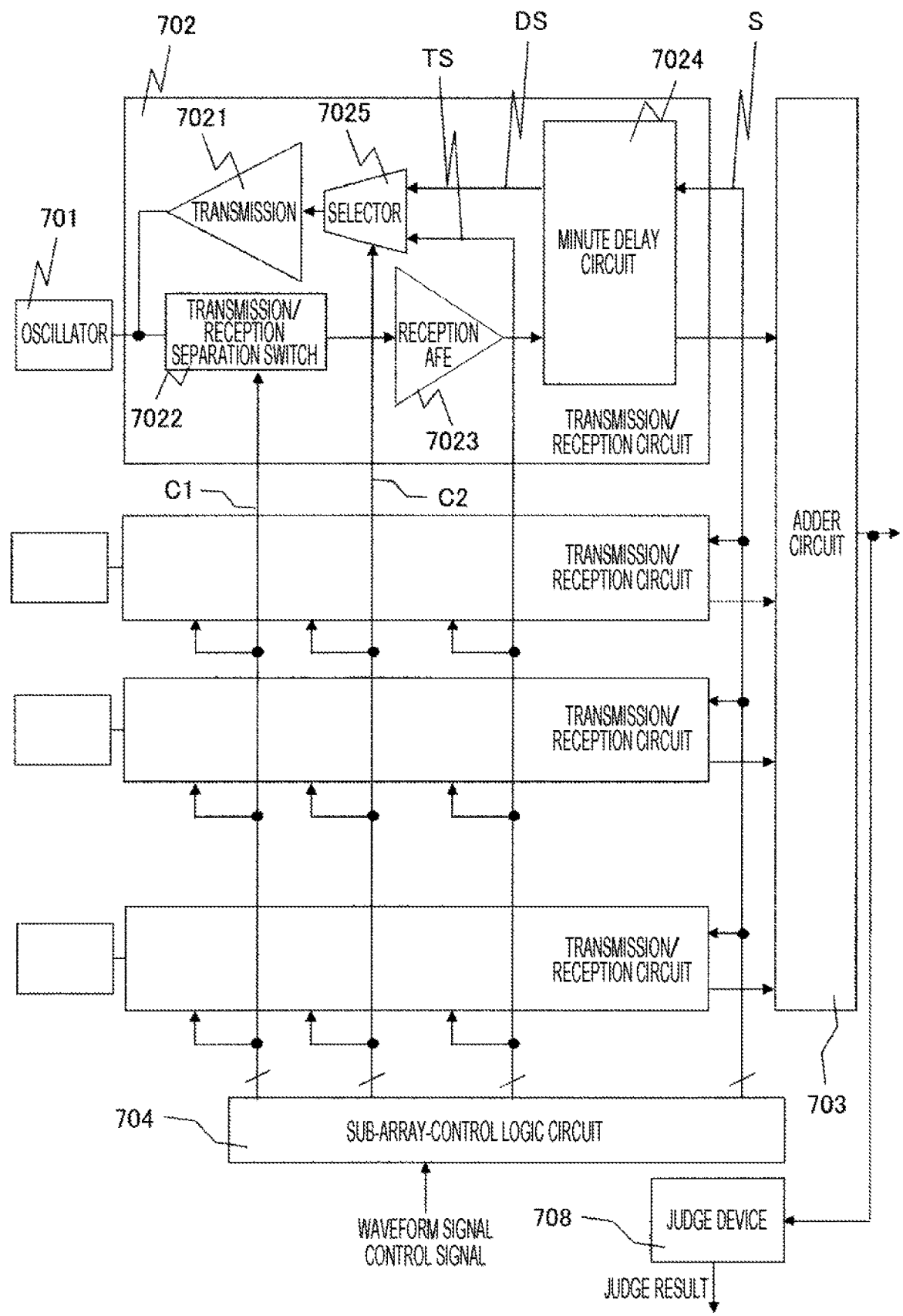
FIG. 9 is a block diagram showing a configuration example including a judge device for judging a result of an internal-signal loopback test in the IC in the sub array of the IC in the ultrasonic-wave probe to which the present invention is applied.

In FIG. 9, a judge device 708 connected to the output of the adder circuit 703 is added to the sub array configuration of FIG. 8. The output of the adder circuit may be buffered and transmitted to the tester or the main-body device to judge whether the operation of the transmission/reception circuit of the oscillator channel in the IC is normal or not according to the waveform by the tester or the main-body device. However, test time can be shortened by integrating a judge circuit in the IC and outputting only the judge result from the IC.

Figure 10:
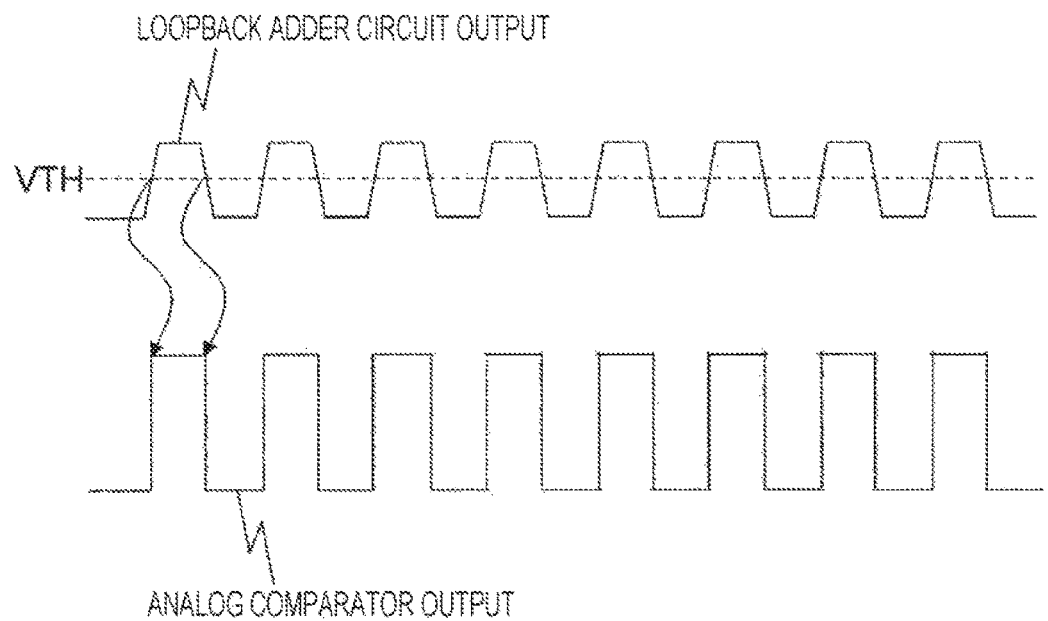
FIG. 10 is a timing chart showing operation principles of the judge device for judging the test result according to the frequency of an internal loopback signal.

FIG. 10 describes principles of the judge device 708. The transmitter carries out transmission in the CW mode and sets a threshold voltage VTH at the middle between the high level and the low level of the output of the loopback adder circuit output through the transmission/reception separation switch, the reception AFE, the minute delay circuit, and the adder circuit. When the output of the loopback adder circuit and VTH are compared by an analog comparator, output of the analog comparator is inverted across VTH every time the output of the loopback adder circuit is toggled; therefore, a logic level signal of the same frequency as the internal loopback signal is obtained. Whether the transmission/reception circuit is operating or not can be judged by counting this by a counter and comparing the number of counts within a certain period, in other words, the frequency with an expected value.

Figure 11:
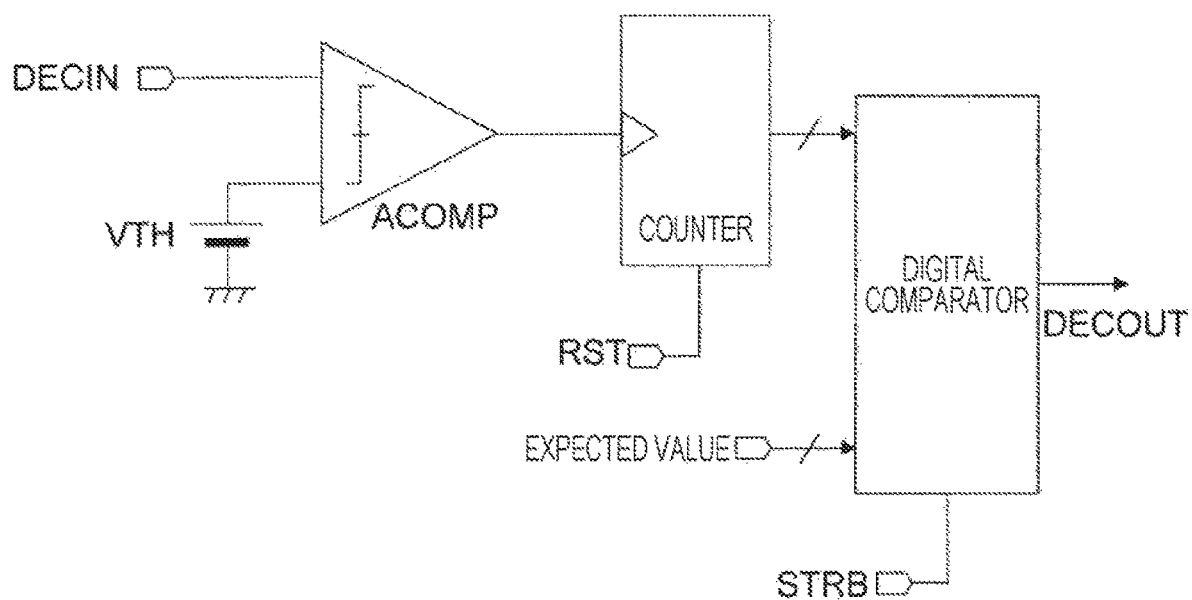
FIG. 11 is a circuit diagram showing a circuit configuration of the judge device for judging the test result according to the frequency of the internal loopback signal.

FIG. 11 shows a configuration of the judge device 708. The device includes an analog comparator ACOMP, which compares the output of the loopback adder circuit input to DECIN with the threshold value VTH; a counter, which receives signals from the analog comparator; and a digital comparator, which compares the count value with the expected value. By resetting the counter with a RST signal, then starting a counter operation, and controlling a strobe signal, the digital comparator retains the known value of counting within a certain period and compares it with the expected value. If it matches the expected value, it is judged that, the transmission/reception circuit is operating, and a test-OK flag is output to DECOUT. If the count value does not match the expected value due to a failure of the transmission/reception circuit or the like, the transmission/reception circuit considers it as a failure and outputs a test-NG flag to DECOUT.

Figure 12:
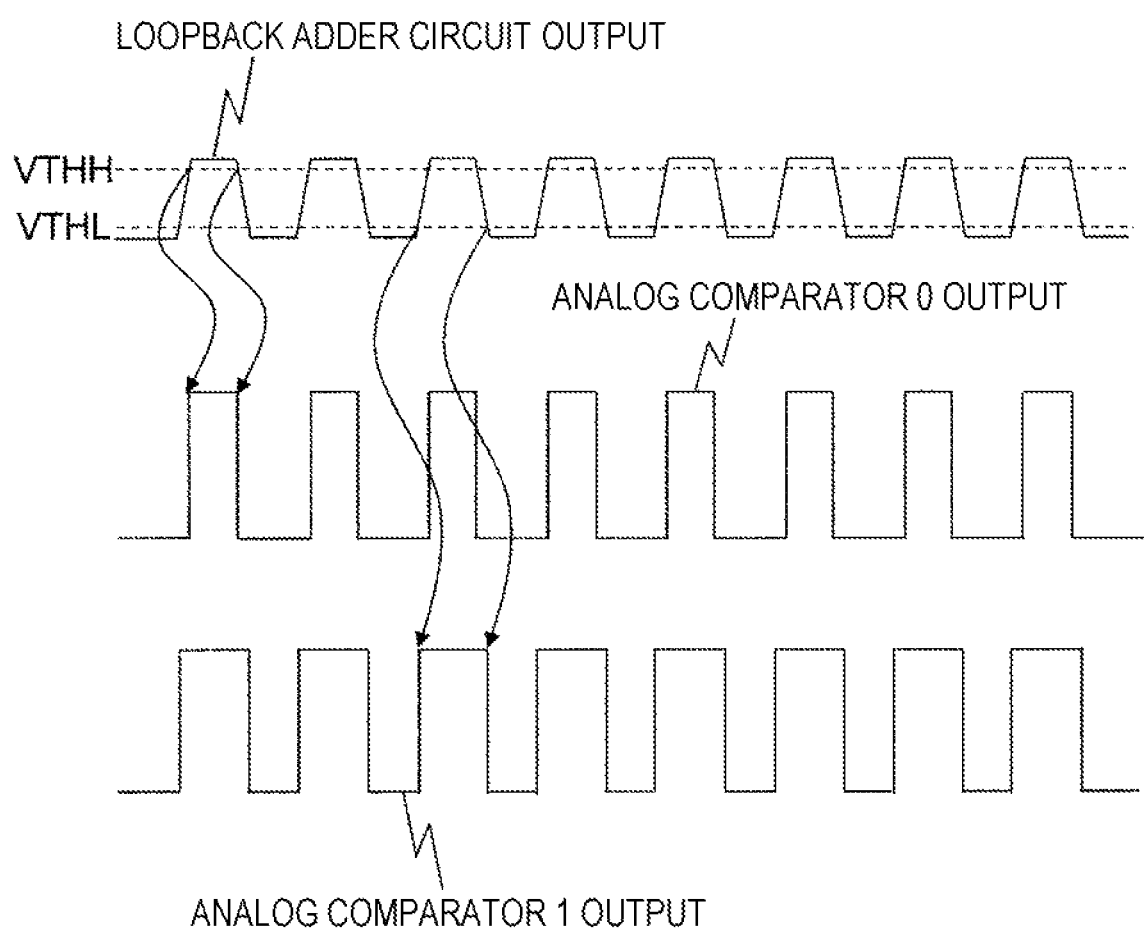
FIG. 12 is a timing chart showing operation principles of the judge device for judging both of the frequency and amplitude of the internal loopback signal.

FIG. 12 describes principles of an improved judge device which judges signal amplitudes and signal frequencies. In the configuration of the judge device of FIG. 11, it is judged whether the circuit is operating at the frequency of the signal or not, but cannot judge whether the amplitude of the signal is equal to or higher than a certain value. Therefore, in FIG. 12, the signal amplitude is also judged by using two types of thresholds VTHH and VTHL. As a high level of the output of the loopback adder circuit, a potential equal to or higher than VTHH is expected, and a potential equal to or lower than VTHL is expected as a low level. An analog comparator 0, which compares the output of the loopback adder circuit with VTHH, and an analog comparator 1, which compares the output of the loopback adder circuit with VTHL, are prepared; and, when a comparison operation is carried out, as shown in FIG. 12, the output of the analog comparator 0 toggles every time the output of the loopback adder output crosses VTHH, and the output of the analog comparator 1 toggles every time the output crosses VTHL. It is expected that the frequencies of the output pulses of the two analog comparators match the frequency of the original loopback adder circuit output signal. For example, if the output of the loopback adder circuit has not reached VTHH due to a fault of the transmission/reception circuit, the output of the analog comparator 0 becomes DC without toggling so that it can be judged that a predetermined signal amplitude is not appearing.

Figure 13:
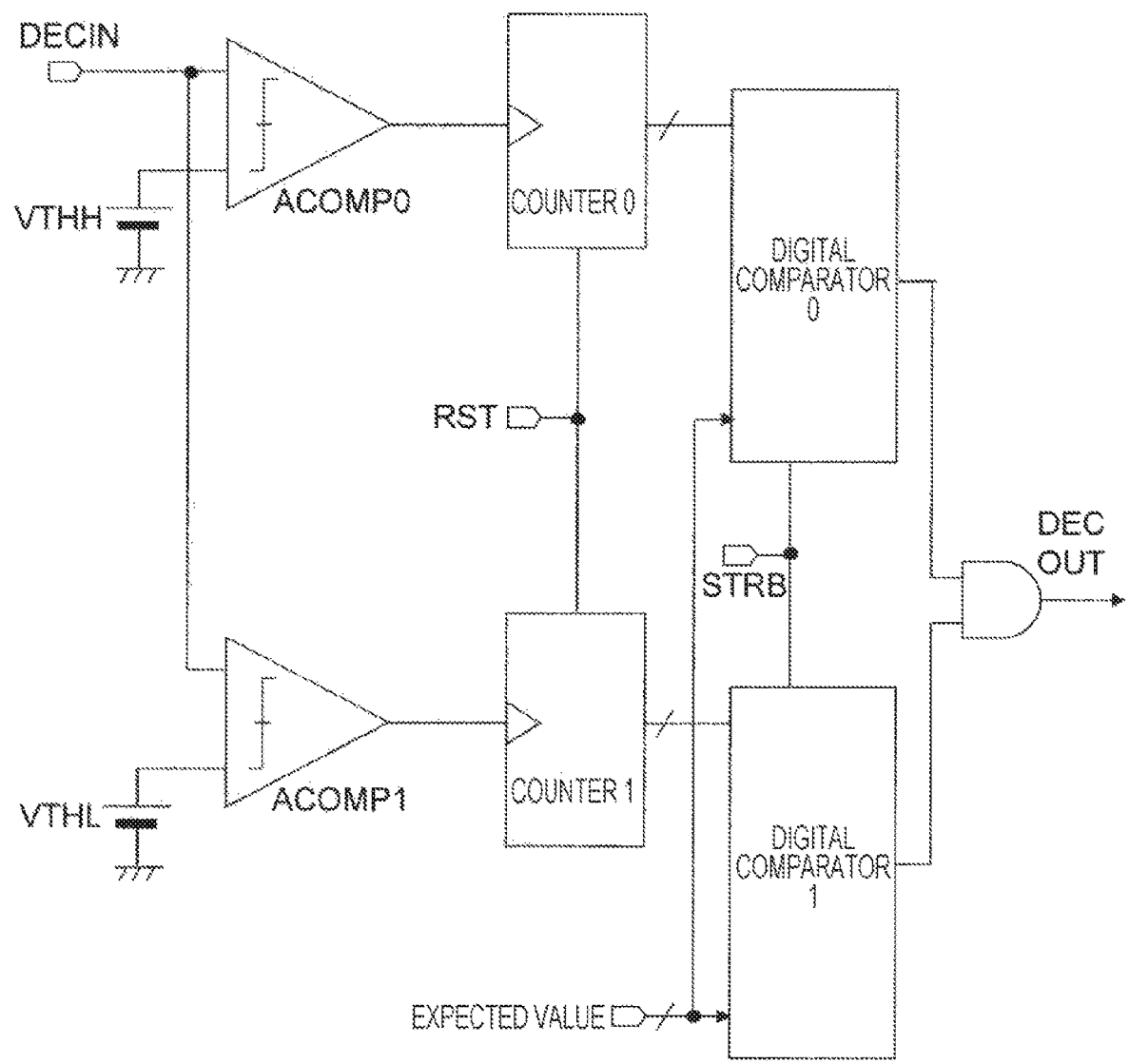
FIG. 13 is a block diagram showing a circuit configuration of the judge device to judge both of the frequency and amplitude of the internal loopback signal.
Figure 14:
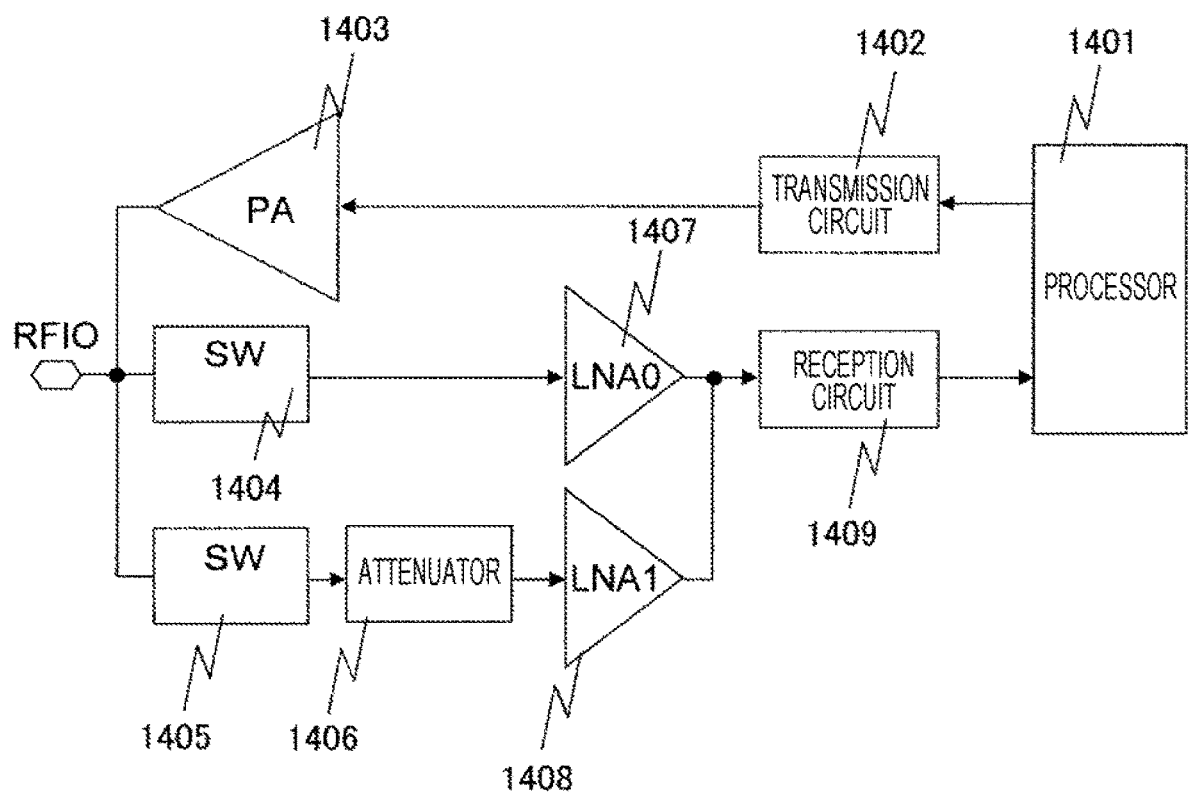
FIG. 14 is a block diagram re-illustrating FIG. 7 of PTL 1 from the viewpoint of the inventors.

FIG. 13 shows a configuration of a judge device which operates according to the principles of FIG. 12. The threshold voltages VTHH and VTHL are prepared, and analog comparators ACOMP0 and ACOMP1, which respectively receive them, are prepared. The outputs of the two analog comparators are respectively counted by a counter 0 and a counter 1 and are compared with an expected values by a digital comparator 0 and a digital comparator 1. If the transmission/reception circuit is normal, it is expected that the number of times the loopback addition output input to DECIN crosses VTHH within a certain period and the number of times it crosses VTHL are the same; therefore, the values of the counter 0 and the counter 1 are compared with the same expected value. Only when the logical product of the outputs of the digital comparator 0 and the digital comparator 1 is obtained and both of the numbers of times that the loopback addition output signal crosses VTHH and VTHL match the expected value, it is judged that the transmission/reception circuit is normal and the frequency and the amplitude of the signal are as expected.

Fourth Embodiment

In the configuration of FIG. 8, the operation in the internal-signal loopback test of the minute delay circuit is assigned to the reception operation, but can be also assigned to a transmission operation.

Figure 15:
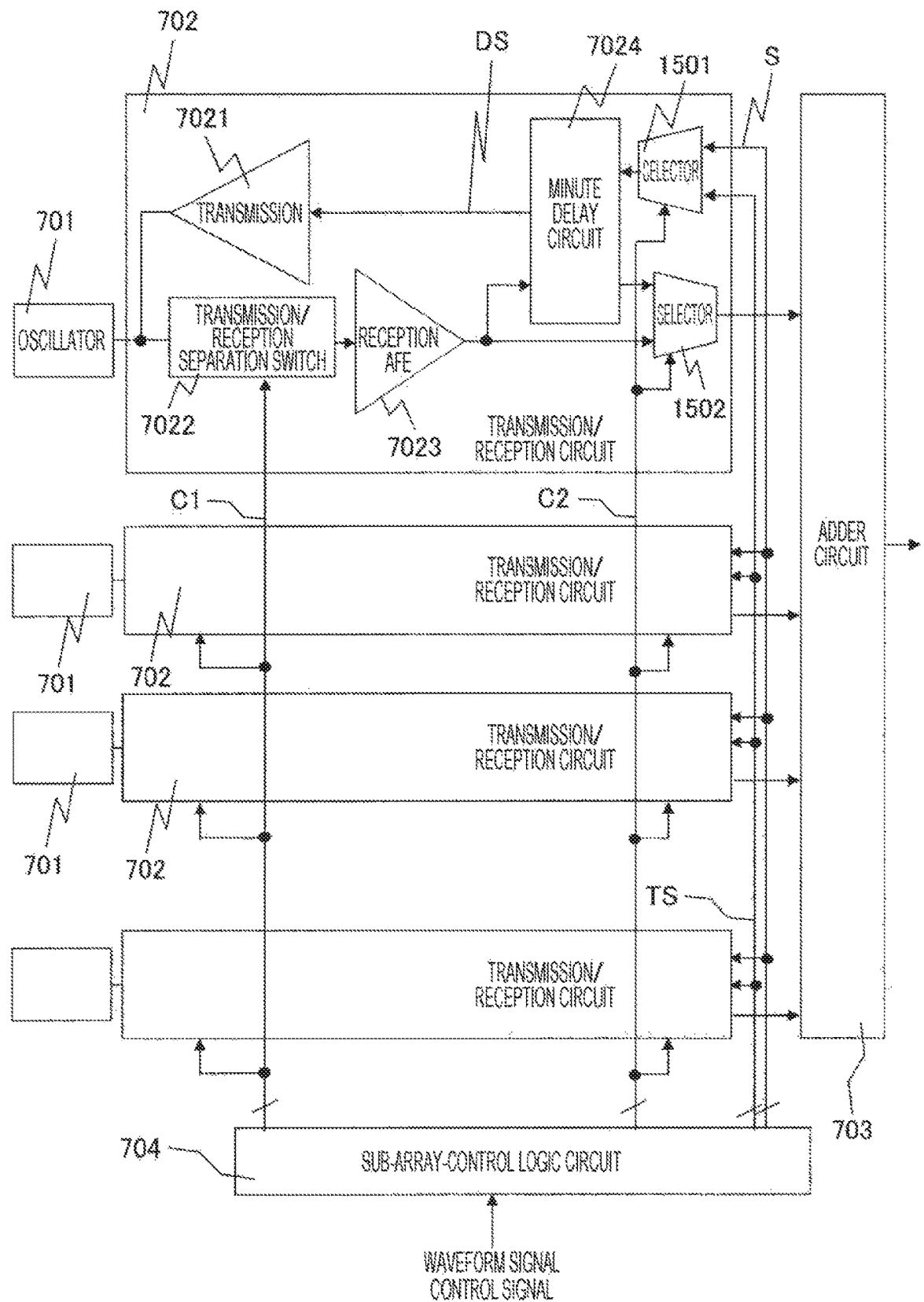
FIG. 15 is a block diagram showing a sub array configuration example of the IC in the ultrasonic-wave probe to which the present invention is applied.

FIG. 15 shows an example in which the operation in the internal-signal loopback test of the minute delay circuit is assigned to the transmission operation.

Only the parts different from FIG. 8 will be described. A selector 1501 inputs the waveform signal S to the minute delay circuit 7024 in the case of normal transmission and selects and inputs the loopback-test waveform signal TS thereto in the loopback test. In addition, a selector 1502 inputs the reception signal to the minute delay circuit 7024 in the case of normal reception and passes the minute delay circuit and inputs that to the adder circuit 703 in the case of loopback test.

As described in the above embodiments, the internal-signal loopback test method in which the switch-off state is obtained in the case of transmission, wherein the reception circuit is separated from the high-voltage drive signal generated by the transmission circuit to prevent electric breakdown; and the switch-on state is obtained in the case of reception, wherein the transmission/reception separation switch circuit which causes the minute reception signal from the oscillator to pass therethrough receives the large-amplitude internal loopback signal from the transmission circuit and attenuates and outputs the signal while ensuring the withstand voltage in the transmission/reception separation switch so that the subsequent low-voltage reception circuit is not destroyed can be realized.

According to the embodiments of the switch circuit, the ultrasonic-wave probe, the ultrasonic-wave diagnosis apparatus, and the test method described above, in a test of a silicon wafer of an IC or a chip after dicing, a realistic test can be realized for each channel of the oscillator at low cost by causing the probes to abut only the signal pads for transmitting/receiving signals to/from the main-body device without causing the probes to abut the many pads connected to the oscillators, and defective chips can be screened. Furthermore, even after mounting on the probe, the transmission/reception circuit can be electrically tested, and failure due to aging deterioration can be diagnosed. In addition, if the present embodiment is used, the internal-signal loopback test method in which the large-amplitude internal loopback signal from the transmission circuit is received, and the signal is attenuated and output while ensuring the withstand voltage in the transmission/reception separation switch so that the subsequent low-voltage reception circuit is not destroyed can be realized. More specifically, the present embodiment exerts effects as the techniques for screening defects of transmission/reception circuits of IC at low cost, without electrically contacting the many terminals connected to the oscillators.

When a test is to be carried out by using the above described embodiment, the test can be carried out in a chip unit at the point when a chip equipped with a transmission/reception circuit, an adder circuit, and the like is manufactured. In this case, the oscillators have not connected yet in some cases. In a case of the test of a single chip, test waveforms may be supplied from a test-waveform generating circuit outside the chip, and judge may be also carried out by a judge circuit outside the chip. Meanwhile, part or all of the test-waveform generating circuit or the judge circuit may be built in the chip in advance. Also, a pre-shipment test may be carried out at the point when the chip is connected to the oscillators and assembled as an ultrasonic-wave probe. Alternatively, after a product of the ultrasonic-wave probe (probe) attached to a diagnosis-apparatus main body is shipped, tests may be periodically carried out during usage by a user (s). For example, the tests can be carried out as the tests periodically carried out by a serviceman or in a test mode automatically activated when the power source of the apparatus is ON. Also in this case, part or all of the test-waveform generating circuit or the judge circuit may be built in the ultrasonic-wave probe or the diagnosis-apparatus main body or may be formed as a test device carried by a serviceman. By virtue of this, not only initial defects, but also failure caused along aging can be also diagnosed.

The present invention is not limited to the above described embodiments, but include various modification examples. For example, part of the configuration of one of the embodiments may be replaced by the configuration of another one of the embodiments, and the configuration of one of the embodiments may include the configuration of another one of the embodiments. In addition, part of the configuration of each of the embodiments can be subjected to addition/deletion/replacement with the configuration of the other embodiments.

The functions of "source" and "drain" of a transistor are sometimes replaced by each other, for example, when a transistor of different polarities is employed or when the directions of currents are changed in circuit operations. Therefore, in the present description, the terms "source" and "drain" can be used by replacing them by each other.

INDUSTRIAL APPLICABILITY

Effects are exerted by mounting on an IC in an ultrasonic-wave probe connected to an ultrasonic-wave diagnosis apparatus.

REFERENCE SIGNS LIST

MN* NMOS
MP* FMOS
C* Capacitor
R* Resistance
INV* Logic inverter
Vdd Power source
SWIN Switch input
SWOUT Switch output
D* Diode
AFE Analog front end
IC Integrated Circuit Integrated Circuit
CW Continuous wave continuous wave

The invention claimed is:
1. An ultrasonic-wave probe comprising:
an oscillator;
a transmission circuit connected to the oscillator;
a reception circuit connected to the oscillator; and
a transmission/reception separation switch disposed between the oscillator and the reception circuit, wherein the transmission/reception separation switch includes two transistor elements, a gate and a source of the two transistor elements are mutually connected,
the transmission/reception separation switch includes a gate-potential step-down circuit configured to lower a voltage Vgs between the common gate and the common source of the two transistor elements, and
the two transistor elements are configured such that in a case that a test signal is input to the transmission circuit to loopback the test signal from the transmission circuit to the reception circuit, a gate potential of the transistor elements is stepped down to cause the test signal to pass through while retaining the voltage Vgs between the common gate and the common source, the voltage Vgs not violating a gate-source withstand voltage of the transistor elements.
2. The ultrasonic-wave probe according to claim 1, wherein
the gate-potential step-down circuit includes at least two resistive elements, and
the voltage Vgs between the common gate and the common source is set by a voltage division ratio of a power-supply voltage and the two resistive elements.
3. The ultrasonic-wave probe according to claim 1, wherein
the gate-potential step-down circuit includes one or a plurality of serially-connected diode elements and includes a resistance or a current source for obtaining a current to flow to the diode(s), and
the voltage Vgs between the common gate and the common source is set by a power-supply voltage and a forward voltage of the diode(s).

4. The ultrasonic-wave probe according to claim 1, wherein
the gate-potential step-down circuit includes one or a plurality of drain-gate-connected diode-connected transistor(s) and includes a resistance or a current source for obtaining a current to flow to the diode-connected transistor(s), and
the voltage Vgs between the common gate and the common source is set by a power-supply voltage and a gate-source voltage of the diode-connected transistor.

5. The ultrasonic-wave probe according to claim 1, wherein
an output-side transistor is connected to a switch output of the transmission/reception separation switch,
a connection destination of the output-side transistor is GND of 0 V or a power source corresponding to a center voltage of a signal applied to an input in a switch-on state, and
the switch output is short-circuited to the GND or the power source corresponding to the center voltage via the output-side transistor to subject a voltage of an input signal of the transmission/reception separation switch to voltage dividing by an on-resistance of the transmission/reception separation switch and an on-resistance of the output-side transistor and attenuate a signal amplitude of the voltage.

6. The ultrasonic-wave probe according to claim 5, wherein
the output-side transistor can be set to exert three or more functions corresponding to modes that:
in a case of reception of the ultrasonic-wave probe, the output-side transistor is in an off-state and causes a switch input signal of the transmission/reception separation switch to pass through without being attenuated;
in a case of transmission of the ultrasonic-wave probe, the output-side transistor is in an on-state and connects the switch output to the GND or the power source corresponding to the center voltage with a low impedance to suppress voltage variation of a switch output signal of the transmission/reception separation switch; and,
when the test signal is to loopback, the output-side transistor becomes an on-state and subjects the input signal of the switch to voltage dividing by the on-resistance of the transmission/reception separation switch and the on-resistance of the output-side transistor.

7. The ultrasonic-wave probe according to claim 1, wherein
potentials in three or more levels are applied as the potential of the common gate of the two transistor elements,
in a case of reception of the ultrasonic-wave probe, the gate-source voltage Vgs is turned on as a first voltage with a low on-resistance,
in a case of transmission of the ultrasonic-wave probe, the gate-source voltage Vgs is caused to be in a switch-off state as a second voltage, and
when the test signal is to loopback, the gate-source voltage Vgs between the first voltage and the second voltage is applied to obtain an on-state with a high on-resistance higher than the low on-resistance, so that a plurality of states in the three or more levels corresponding to the modes are obtained.

8. An ultrasonic-wave diagnosis apparatus comprising: a sub array(s); an adder circuit configured to add an output from the sub array; and a main-body device configured to process the output from the adder circuit, wherein the sub array includes a plurality of oscillator channels,
each of the oscillator channels includes an oscillator, a transmission circuit connected to the oscillator, a reception circuit connected to the oscillator, and a transmission/reception separation switch,
the transmission/reception separation switch includes a transistor element as a switching element,
the transmission/reception separation switch includes a potential control circuit for controlling a gate-source voltage Vgs of the transistor, and
the ultrasonic-wave diagnosis apparatus includes:
a transmission mode to cause the transmission/reception separation switch to be in an off-state in a case of transmission in which a signal from the transmission circuit is input to the oscillator;
a reception mode to cause the transmission/reception separation switch to be in an on-state in a case of reception in which a signal is input from the oscillator to the reception circuit; and
a test mode to set the gate-source voltage Vgs of the transistor to a potential different from the potential in the transmission mode and the potential in the reception mode by the potential control circuit.

9. The ultrasonic-wave diagnosis apparatus according to claim 8, wherein,
in the test mode, transmission of a continuous-wave Doppler mode with a transmission voltage lowered than a B mode is carried out by the transmission circuit.

10. The ultrasonic-wave diagnosis apparatus according to claim 8, wherein,
in the test mode, a test signal passed through the transmission circuit, the transmission/reception separation switch, and the reception circuit is transmitted to the main-body device, and the transmitted signal is compared with an expected pattern by the main-body device.

11. The ultrasonic-wave diagnosis apparatus according to claim 8, comprising
an ultrasonic-wave probe including the plurality of sub arrays, wherein,
in the test mode, a test signal passed through the transmission circuit, the transmission/reception separation switch, and the reception circuit is compared with an expected pattern in the ultrasonic-wave probe.

12. The ultrasonic-wave diagnosis apparatus according to claim 8, comprising
a judge device configured to compare, with an expected pattern, and judge a test signal passed through the transmission circuit, the transmission/reception separation switch, and the reception circuit in the test mode, wherein
the judge device compares a frequency of a voltage signal of the passed test signal with an expected value.

13. The ultrasonic-wave diagnosis apparatus according to claim 8, comprising
a judge device configured to compare, with an expected pattern, and judge a test signal passed through the transmission circuit, the transmission/reception separation switch, and the reception circuit in the test mode, wherein
the judge device includes
two or more analog comparators configured to compare a voltage of the passed test signal with predetermined reference potentials,
the reference potentials input to the respective analog comparators are different from each other, and the judge device compares, with an expected value, both of:
the number of times that the voltage crosses a higher reference potential among the two reference potentials and is toggled within predetermined time, in other words, a frequency of the signal in a case of slicing with a high threshold value and
the number of times that the voltage crosses a lower reference potential among the two reference potentials and is toggled within predetermined time, in other words, a signal frequency in a case of slicing with a low threshold value
to judge that the voltage has reached a voltage level equal to or higher than the high reference potential and a voltage level equal to or less than the low reference potential and the test signal is toggled at a predetermined frequency with an amplitude equal to or more than a difference between the reference potentials.

14. A test method of an ultrasonic-wave probe that includes an oscillator; a transmission circuit connected to the oscillator; a reception circuit connected to the oscillator; and a transmission/reception separation switch disposed between the oscillator and the reception circuit, wherein the transmission/reception separation switch includes two transistor elements and is configured to mutually connect a gate and a source of the two transistor elements, the test method comprising:
causing, in a transmission mode, the transmission/reception separation switch to be in an off-state in a case of transmission in which the oscillator is driven by the transmission circuit;
causing, in a reception mode, the transmission/reception separation switch to be in an on-state in a case of reception in which a signal from the oscillator is input to the reception circuit; and
setting, in a test mode, a voltage Vgs between the common gate and the common source of the two transistors to a middle of a voltage in the transmission mode and a voltage in the reception mode.

15. The test method of the ultrasonic-wave probe according to claim 14, wherein
a voltage applied between the common gate and the common source of the two transistors is subjected to voltage dividing or voltage step-down to change the voltage Vgs and make a transition among the three modes.

* * * * *